(12) United States Patent
Cottone (10) Patent No.: US 11,524,144 B2
(45) Date of Patent: Dec. 13, 2022

(54) BALLOON ANCHORING GUIDE CATHETER EXTENSION

(71) Applicant: ORBUSNEICH MEDICAL PTE. LTD., Singapore (SG)

(72) Inventor: Robert J. Cottone, Davie, FL (US)

(73) Assignee: ORBUSNEICH MEDICAL PTE. LTD., Singapore (SG)

( * ) Notice: Subject to any disclaimer, the term of this patent is extended or adjusted under 35 U.S.C. 154(b) by 0 days.

(21) Appl. No.: 16/909,320

(22) Filed: Jun. 23, 2020

(65) Prior Publication Data

US 2020/0398028 A1    Dec. 24, 2020

Related U.S. Application Data

(60) Provisional application No. 62/865,498, filed on Jun. 24, 2019.

(51) Int. Cl.
*A61M 25/04*    (2006.01)
*A61M 25/01*    (2006.01)

(52) U.S. Cl.
CPC ........ *A61M 25/04* (2013.01); *A61M 25/0113* (2013.01); *A61M 2205/0266* (2013.01)

(58) Field of Classification Search
CPC .............. A61M 25/04; A61M 25/0113; A61M 2025/0079; A61M 25/1011; A61M 25/0662
See application file for complete search history.

(56) References Cited

U.S. PATENT DOCUMENTS

| | | | |
|---|---|---|---|
| 5,792,118 A | 8/1998 | Kurth et al. | |
| 6,135,981 A * | 10/2000 | Dyke | A61M 25/1011 604/101.01 |
| 2005/0090852 A1* | 4/2005 | Layne | A61F 2/4601 604/103.05 |
| 2014/0052097 A1 | 2/2014 | Petersen et al. | |
| 2014/0249508 A1 | 9/2014 | Wang et al. | |
| 2016/0051799 A1 | 2/2016 | Daniels et al. | |
| 2016/0175569 A1* | 6/2016 | Heuser | A61M 25/0054 604/509 |
| 2016/0346515 A1 | 12/2016 | Buller et al. | |
| 2017/0105743 A1 | 4/2017 | Yale et al. | |
| 2017/0252043 A1* | 9/2017 | Fuller | A61B 17/12136 |

FOREIGN PATENT DOCUMENTS

EP    3 498 329 A1    6/2019
WO    2017/019900 A1    2/2017

OTHER PUBLICATIONS

International Search Report and Written Opinion of corresponding PCT/US2020/039086, dated Sep. 10, 2020.
European Search Report and Written Opinion of corresponding EP 20 18 2056, dated Nov. 18, 2020.

* cited by examiner

*Primary Examiner* — Bhisma Mehta
*Assistant Examiner* — Rachel T. Smith
(74) *Attorney, Agent, or Firm* — Leason Ellis LLP (57) ABSTRACT

A guide catheter extension, having a push member having a proximal end and a distal end; a tube frame coupled to the distal end of the push member, the tube frame defining a lumen having a diameter sufficient to receive an interventional vascular device therethrough; and an inflatable element coupled to the tube frame, wherein the inflatable element is expandable into the lumen.

6 Claims, 11 Drawing Sheets

BALLOON ANCHORING GUIDE CATHETER EXTENSION

FIELD OF THE INVENTION

The present disclosure relates to systems and methods of use thereof for capturing or securing intravascular devices.

BACKGROUND OF THE INVENTION

In coronary artery disease, the coronary arteries may be narrowed or occluded by atherosclerotic plaques or other lesions. These lesions may totally obstruct the lumen of the artery or may dramatically narrow the lumen of the artery. In order to diagnose and treat obstructive coronary artery disease, it is commonly necessary to pass a guidewire or other interventional instruments through and beyond the occlusion or stenosis of the coronary artery.

Percutaneous coronary intervention (PCI), also known as coronary angioplasty, is a therapeutic procedure used to treat the narrowed or stenotic section of the coronary artery of the heart due to coronary lesions or obstructions. A guide catheter may be used in PCI to support easier passage for another catheter or interventional device, such as, a microcatheter, stents or balloons, to access the target site. For example, the guide catheter can be inserted through the aorta and into the ostium of the coronary artery. Once seated in the opening or ostium of the coronary artery a guidewire or other instrument can be passed through the lumen of the guide catheter and then inserted into the artery distal to the occlusion or stenosis.

However, guide catheters may encounter certain difficulties. The anatomy in the area for placement, e.g., the coronary vasculature, may be tortuous and the lesions themselves may be comparatively non-compliant. Moreover, when crossing comparatively non-compliant lesions, a backward force sufficient to dislodge the guide catheter from the ostium of the artery being treated can be generated. In order to improve backup support, guide catheter extension devices may be employed to facilitate placement and approach of one or more treatment devices in and around a stenotic region.

For example, when treating a chronic total occlusion ("CTO"), certain techniques employ multiple devices to approach the CTO both from antegrade and retrograde directions. Either of these techniques, or other similar procedures, involve routing and controlling multiple devices in and around a guide catheter and guide catheter extension device in prolixity to a CTO or other physiological condition/region. The present disclosure provides devices and methods of use thereof for selectively securing one or more medical devices in and around a guide catheter extension for such procedures.

SUMMARY OF THE INVENTION

The present invention advantageously provides a guide catheter extension, comprising: a push member having a proximal end and a distal end; a tube frame coupled to the distal end of the push member, the tube frame defining a lumen having a diameter sufficient to receive an interventional vascular device therethrough; and an inflatable element coupled to the tube frame, wherein the inflatable element is expandable into the lumen. The inflatable element may be expandable to occupy between 10% and 90% of a cross-sectional area of the lumen. The inflatable element may be expandable outward beyond an exterior surface of the tube frame. The tube frame may define a window therein through which the inflatable element is expandable outward beyond an exterior surface of the tube frame. The push member may include an inflation lumen in fluid communication with an interior of the inflatable element. At least a portion of the inflation lumen may define an arcuate cross-section having a radius of curvature equal to a radius of the lumen of the tube frame. The guide catheter extension may include a tongue element extending from a proximal segment of the tube frame, wherein the tongue element is directly coupled to the distal region of the push member.

A guide catheter extension is disclosed, including a push member having a proximal end and a distal end; a tube frame coupled to the distal end of the push member, the tube frame defining a lumen having a diameter sufficient to receive an interventional vascular device therethrough; a first inflatable element coupled to the tube frame, wherein the first inflatable element is expandable into the lumen; and a second inflatable element coupled to the tube frame, wherein the second inflatable element is expandable outward beyond an exterior surface of the tube frame. The first inflatable element may be expandable to occupy between 10% and 90% of a cross-sectional area of the lumen. The first and second inflatable elements may be independently expandable. The push member may include a first inflation lumen in fluid communication with an interior of the first inflatable element. At least a portion of the first inflation lumen may define an arcuate cross-section having a radius of curvature equal to a radius of the lumen of the tube frame. The push member may include a second inflation lumen in fluid communication with an interior of the second inflatable element.

A guide catheter extension is provided, having a push member having a proximal end and a distal end; a tube frame coupled to the distal end of the push member, the tube frame defining a lumen having a diameter sufficient to receive an interventional vascular device therethrough; and an inflatable element movably coupled to the push member. The inflatable element may be movable along a longitudinal axis of the push member. The inflatable element may be coaxially mounted on the push member. The guide catheter extension may include an inflation lumen in fluid communication with an interior of the inflatable element, wherein the inflation lumen is coaxial with the push member. The inflatable element may be expandable to a size between 10% and 90% of a cross-sectional area of the lumen of the tube frame.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION OF THE INVENTION

The present disclosure provides systems, devices, and methods of use thereof for capturing and/or securing intravascular devices within the anatomy which may include, for example, securing or capturing a guidewire or other minimally-invasive intravascular devices during the assessment and/or treatment of chronic total occlusions ("CTO"). Such assessment and/or treatment of chronic total occlusions may include, for example, CART, reverse CART, and other techniques that employ multiple devices to approach a CTO both from antegrade and retrograde directions and include the desire to capture or secure the devices in place during use.

Now referring to the figures, an example of an intravascular device in the form of a guide catheter extension 1000 is shown that can be used to secure or capture one or more guidewires and/or other minimally-invasive intravascular devices during a medical procedure to assess and/or treat occlusions or other vascular defects or conditions. The guide catheter extension 1000 is sized and configured to pass through and extend distally from a guide catheter 'GC' as described herein. The guide catheter extension 1000 generally includes a push member 1001 coupled to a distal tube frame 1005, and may have sufficient length such that, in use, a proximal region of the guide catheter extension 1000 is accessible or positioned exterior to a patient (such as at a proximal end or hub of a separate guide catheter), while a distal region of the guide catheter extension 1000 extends distally outward from an end of the guide catheter positioned within the anatomy of the patient.

The push member 1001 may include, for example, one or more segments of hypotube, spiral-cut hypotube, multi-thread cable, interrupted-spiral cut tube, other cut geometries/configurations, or other elongated member(s), and may include one or more lumens 1002 therein and/or therethrough for the passage of one or more wires, devices, fluid delivery and/or aspiration features, or the like.

The push member 1001 may include a small diameter or cross-sectional profile relative to an inner diameter or clearance of the guide catheter to reduce the amount of space within the guide catheter that the push member 1001 occupies, thereby allowing one or more other devices, instruments, or otherwise to pass through the guide catheter with minimal interference or obstruction. For example, the push member 1001 may have a diameter or cross-sectional width between approximately 0.254 mm (0.010 inches) and approximately 2.54 mm (0.100 inches) for use in a guide catheter having an inner diameter of 1.1016-30.48 mm (0.04-1.20 inches). In a preferred example, the push member 1001 may have a diameter or cross-sectional width between approximately 0.254 mm (0.010 inches) and approximately 0.762 mm (0.030 inches). The push member 1001 may have one or more cross-sectional shapes or profiles along its length, including but not limited to circular, hemi- or semi-circular, square, rectangular, triangular, and/or oval shapes or profiles. In addition and/or alternatively, the push member 1001 can comprise a plurality of cut patterns in one or more sections thereof.

The push member 1001 may define an overall length constituting the majority of the length of the guide catheter extension 1000. The length of the push member 1001 may be sufficient to enter an incision or patient access point (which may include, for example, a hub, hemostatic valve, and the like), traverse the vasculature of the patient, and position the tube frame 1005 in proximity to a desired treatment site while a portion of the push member 1001 remains outside the patient and accessible/operable by a physician. The length may vary depending upon the particular procedure or application being performed and/or a vasculature access point being utilized (e.g., whether introduced via a radial artery, femoral artery, contralateral access, or the like). The push member and/or other proximal portion of the guide catheter extension 1000 may include a stop feature that prevents a physician from inserting the extension 1000 too far into the guide catheter. For example, the guide catheter extension 1000 may include a raised protrusion, weld, or other mass that exceeds a diameter or size of a guide catheter, hemostatic valve, and/or proximal device hub to mechanically prevent the over-insertion of the guide catheter extension 1000.

The tube frame 1005 includes or otherwise defines an outer wall 1007 and an inner wall 1006 enclosing a lumen 1008 having a diameter sufficient to receive an interventional vascular device therethrough, a proximal end 1012, and a distal end 1013. The tube frame 1005 has a plurality of cut patterns 1015, 1016 therein (of note, 1015 and 1016 represent only two possible embodiments of the various cut patterns that can be present in the tube frame).

The tube frame 1005 may be constructed from nitinol or stainless steel. For example, the tube frame can be made from metals, polymers, or a combination of polymers and metals. Examples of materials that may be used include stainless steel (SST), nickel titanium (Nitinol), or polymers. Preferred examples of other metals which may be used include, super elastic nickel titanium, shape memory nickel titanium, Ti—Ni, nickel titanium, approximately, 55-60 wt. % Ni, Ni—Ti—Hf, Ni—Ti—Pd, Ni—Mn—Ga, Stainless Steel (SST) of SAE grade in the 300 to 400 series e.g., 304, 316, 402, 440, MP35N, and 17-7 precipitation hardened (PH) stainless steel, other spring steel or other high tensile strength material or other biocompatible metal material. In one preferred embodiment, the material is superelastic or shape memory (e.g., nickel titanium), while in another preferred embodiment, the material is stainless steel.

The tube frame 1005 can include a superelastic alloy (generally referred to as "a shape-memory alloy") in its entirety, or in only in selected sections thereof. Examples of such superelastic alloys include: Elgiloy® and Phynox®, spring alloys, SAE grade 316 stainless steel and MP35N (Nickel Cobalt), and superelastic Nitinol.

Alternatively, the tube frame may be formed from polymers, e.g., include polyimide, PEEK, nylon, polyurethane, polyethylene terephthalate (PET), latex, HDHMWPE (high density, high molecular weight polyethylene) and thermoplastic elastomers or other polymers with similar mechanical properties.

The tube frame 1005 may be made by forming a pipe of a super elastic metal and then removing the parts of the pipe where the notches or holes are to be formed. The notches, holes or cuts can be formed in the pipe by laser (solid-state, femtosecond laser, or YAG laser, for example), electrical discharge (electrical discharge machining (EDM)), chemical etching, photo-etching mechanical cutting, or a combined use of any of these techniques.

A portion of the tube frame 1005 can have a polymer liner and/or the outer wall of the tube frame 1005 can be covered (completely, partially, and/or intermittently) with an outer jacket.

The tube frame 1005 has a tongue element 1017 extending from the proximal end 1012 of the tube frame 1005, and the tongue element 1017 is coupled to the push member 1001. The tongue element 1017 may be unitary with and be formed from the same material composition as the tube frame 1005. A distal end or region of the tongue element 1017 may be positioned distally to the proximal opening of the tube frame 1005, while a proximal end or region of the tongue element 1017 extends proximally past the proximal opening of the tube frame 1005.

The proximal end 1012 of the tube frame 1005 may include a flare or flange 1019 that can be used to close or reduce the gap between the tube frame 1005 and the guide catheter GC.

Additional features and characteristics of the guide catheter extension 1000, including the push member 1001, the distal tube frame 1005, and other components, are set forth in U.S. Patent Application Ser. No. 62/729,282, entitled 'GUIDE CATHETER EXTENSION PLATFORM,' the entirety of which is incorporated herein by reference.

The guide catheter extension 1000 may include one or more inflatable elements 1020 positioned within the lumen 1008 of the distal tube frame. The inflatable element(s) 1020 may include one or more balloons, bladders, or other component that is expandable upon the introduction of a fluid therein. The inflatable element may be formed in a variety of shapes, and may include symmetrical, asymmetrical, or other contoured or geometrical configurations. The inflatable element(s) 1020 may include compliant and/or non-compliant surfaces and/or components, which may for example, be constructed from silicone, nylon, pebax, and/or other polymers.

In the example illustrated in FIGS. 1-6, the inflatable element 1020 is disposed on or about the inner wall 1006 towards the distal end 1013 of the tube frame 1005. The inflatable element 1020 is situated and operable to expand within the lumen 1008 of the distal tube frame 1005. Accordingly, the inflatable element 1020 may be adhered or otherwise positioned directly onto an inner wall 1006 of the distal tube frame.

In the example illustrated in FIGS. 7-12, the inflatable element 1020 is disposed on or about the inner wall 1006 towards the distal end 1013 of the tube frame 1005, and the inflatable element 1020 is situated and operable to expand both within the lumen 1008 of the distal tube frame 1005, and into the space between the guide catheter extension 1000 and the surrounding, external guide catheter GC. To accommodate such expansion characteristics, a portion of the wall of the distal tube frame 1005 may be cut to form a window or space allowing the inflatable element 1020 to expand both inwards within the lumen 1008 and outwards towards the guide catheter GC.

The inflatable element 1020 may include a single internal cavity to expand both into the lumen 1008 and outside of the diameter or outer wall of the tube frame 1005 and into the space between the guide catheter extension 1000 and the guide catheter GC. In an alternative example, the inflatable element 1020 may include multiple inner cavities and/or reservoirs that are independently inflatable such that the portion of the inflatable element 1020 that expands into the lumen 1008 is controllable inflatable independently and separately from the portion of the inflatable element 1020 that expands outside of the diameter or outer wall of the tube frame 1005. The separate portions of the inflatable element 1020 may have independent inflation lumens to provide independent operation. In another example, multiple separate inflatable elements may be employed to provide the independent inflation within the lumen 1008 and outside of the tube frame 1005.

In use, the inflatable element 1020 may be transitionable from a first state in which the inflatable element is substantially planar, flat, and/or otherwise uninflated to a second state where the inflatable element 1020 is inflated, and expands to occupy a substantial portion of the diameter of the lumen 1008 of the distal tube frame, less the cross-sectional area of any devices running therethrough. For example, the inflated inflatable element may provide the expansion capacity to occupy between approximately 10% and approximately 90% of the cross-sectional area of the lumen 1008. The particular expansion needed for a particular procedure may vary depending on the number and dimensions of the auxiliary devices that a physician is entrapping or securing within the lumen 1008. If a single device with a relatively small diameter is being secured, then a larger expansion of the inflatable element 1020 may be employed. In contrast, a lesser degree of expansion of the inflatable element 1020 will be required to secure multiple devices having large cross-sectional areas within the lumen 1008. The expansion and/or conformance of the inflatable element 1020 may vary along the longitudinal length of the of the inflatable element 1020 to accommodate varying dimensions of the devices being secured in the lumen 1008 (e.g., for example, should one or more of the captured devices have a varying cross-section or external dimensions along a length thereof).

In an example where a portion of the inflatable element 1020 expands outwards into the space between the guide catheter GC and the guide catheter extension 1000, the inflatable element 1020 may be expanded to substantially fill the cross-sectional space between the guide catheter GC and the guide catheter extension 1000, as described further herein.

The inflatable element 1020 is in fluid communication with the lumen 1002 of the push member 1001, which may be used as a channel to introduce an inflation medium (such as air, saline, distilled water, or otherwise) into the inflatable element 1020. The inflatable element 1020 may be directly coupled to the push member 1001, or may alternatively couple to the push member 1001 through an intermediary inflation spout or channel 1021 that extends through a portion of the distal tube frame 1005 and extends outwards to connect to the push member 1001 in a proximal direction, while also coupling the inflatable element 1020 in a distal direction. In the illustrated example, the intermediary inflation channel 1021 has a low cross-sectional profile, and a curvature complementary to that of the lumen 1008, to avoid substantially obstructing or reducing the operating diameter of the lumen 1008 and the resultant ability to pass other devices or instruments therethrough. A portion of the wall thickness of the tube frame 1005 may be reduced to create a groove to further accommodate the intermediary inflation spout or channel 1021 and to further avoid substantially obstructing or reducing the operating diameter of the lumen 1008.

The inflatable element(s) 1020 may be expanded by the introduction of a fluid therein, which may be provided at a proximal hub or injection port (not shown) on the guide catheter extension 1000. Controllable expansion of the inflatable element 1020 may be facilitated by a pump, syringe, media cartridge, or other fluid introduction mechanisms employed in vascular procedures, and may be monitored through one or more sensors, medical imaging modalities, or the like.

In one example of use, the guide catheter extension 1000 may be used to capture and secure one or more auxiliary devices within the vasculature of a patient. For example, when treating a CTO, certain techniques employ multiple devices to approach the CTO both from antegrade and retrograde directions. In the CART technique, a guidewire is directed antegrade towards the CTO lesion, while a retrograde balloon device is advanced into the CTO lesion to make a crack or opening. In the reverse-CART technique, the creation of a subintimal crack is conducted by an antegrade balloon at the proximal part of the CTO lesion, while a guidewire approaches distally and retrograde of the lesion. In either of these techniques, or other procedures involving multiple devices in and around a CTO or other physiological condition/region, the guide catheter extension 1000 may be used to secure the distal end of the targeted auxiliary device(s), which may include a retrograde balloon device in the CART technique and/or a retrograde guidewire in the reverse CART technique. In other situations, it may be desired to capture one or more device portions in antegrade and/or retrograde regions of a CTO.

FIGS. 13-18 illustrate such an example of use, where a plurality of auxiliary devices 1022a, 1022b, 1022c (collectively, 'auxiliary devices 1022') are at least partially positioned within the inner lumen 1008 of the distal tube frame 1005, and secured in place by the expanded inflatable element 1020. The illustrated example shows the auxiliary devices 1022 extending completely through the distal tube frame 1005, however, it is contemplated that the length and position of antegrade and/or retrograde auxiliary devices 1022 relative to the distal tube frame may vary so long as there is sufficient overlap between the auxiliary devices 1022 and the inflatable element 1020 to secure the devices within the lumen 1008. In the embodiment where the inflatable element 1020 expands exterior to the distal tube frame 1005 and into the space between the external guide catheter GC and the guide catheter extension 1000, the expansion of the inflatable element 1020 will secure both the relative position of the auxiliary devices 1022 within the lumen 1008 as well as securing the relative position of the guide catheter extension 1000 within the guide catheter GC. The relatively distal location of the inflatable element 1020 allows a physician to capture devices within the lumen 1008 with minimal and/or reduced length of the auxiliary devices 1022 required to enter the guide catheter extension 1000, and eliminates the need to entrain the auxiliary devices 1022 further proximal into the external guide catheter GC itself. This reduces the maneuvering and navigation required by a physician to secure the auxiliary devices 1022 compared to other devices which may entrain and trap auxiliary devices within the GC.

Figure 1:
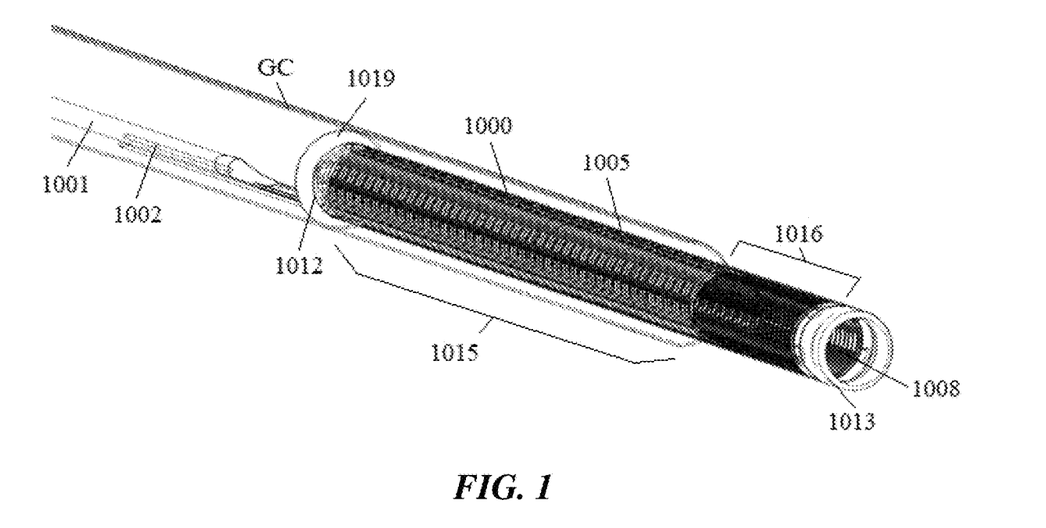
FIG. 1 is an illustration of an example of a vascular device constructed in accordance with the principles of the present disclosure.
Figure 2:
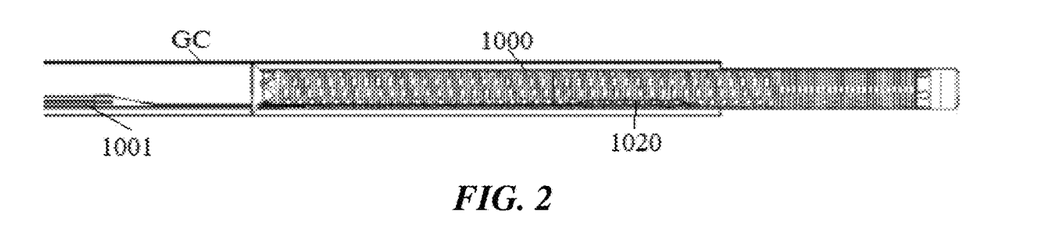
FIG. 2 is a side view of the device shown in FIG. 1.
Figure 3:
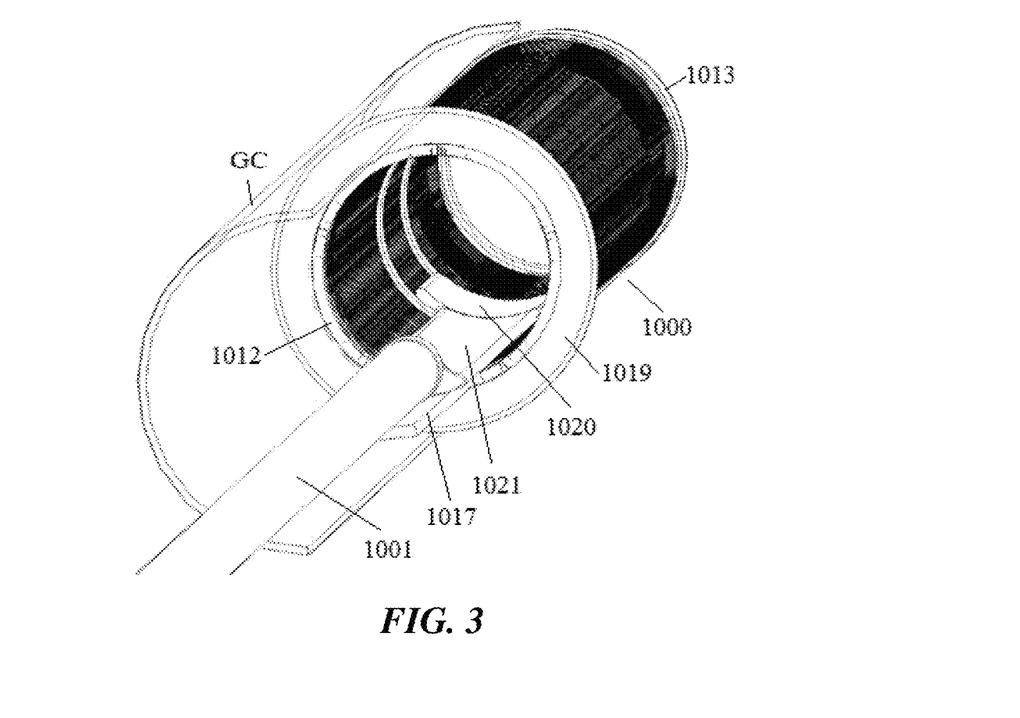
FIG. 3 is a proximal perspective view of the device shown in FIG. 1.
Figure 4:
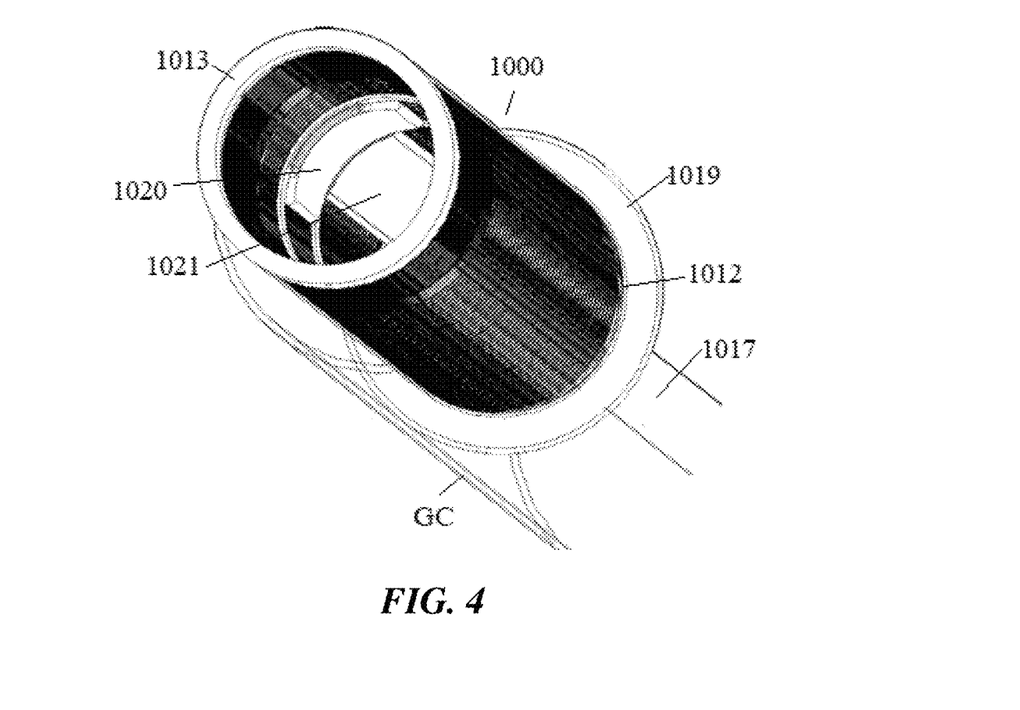
FIG. 4 is a distal perspective view of the device shown in FIG. 1.
Figure 5:
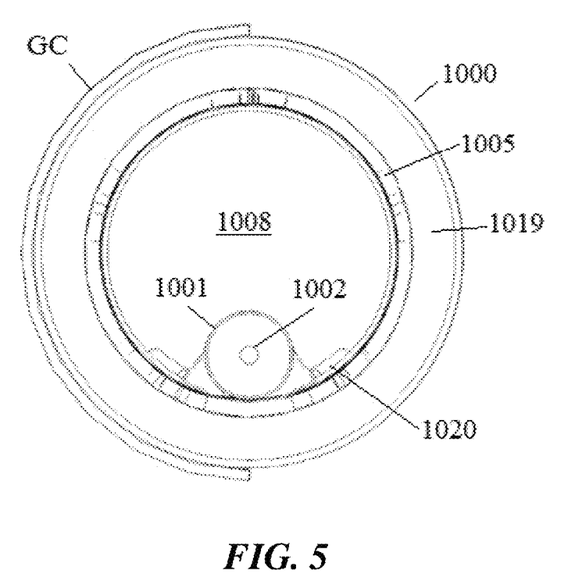
FIG. 5 is a proximal end view of the device shown in FIG. 1.
Figure 6:
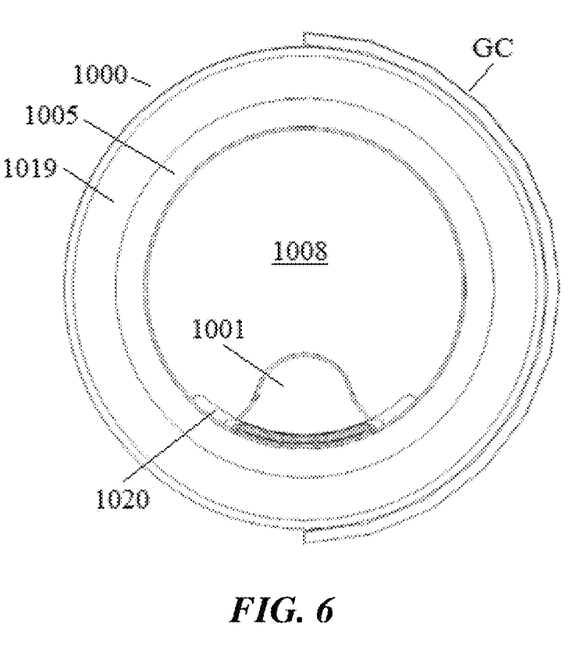
FIG. 6 is a distal end view of the device shown in FIG. 1
Figure 7:
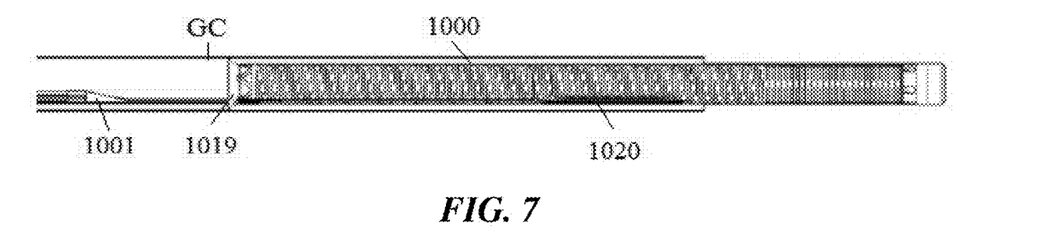
FIG. 7 is an illustration of another example of a vascular device constructed in accordance with the principles of the present disclosure.
Figure 8:
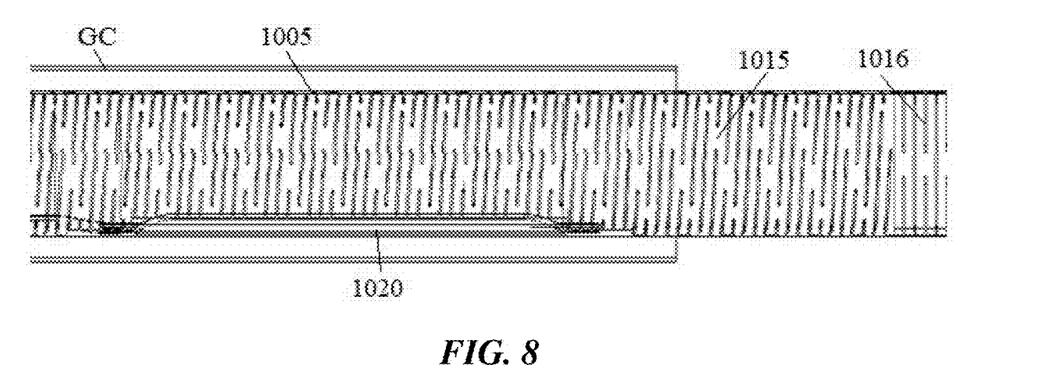
FIG. 8 is a closer side view of the device shown in FIG. 7.
Figure 9:
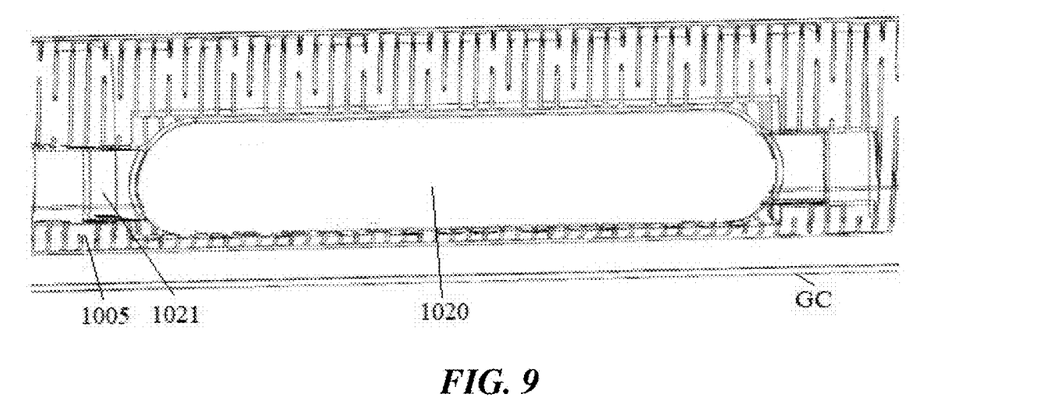
FIG. 9 is an underside view of the device shown in FIG. 7.
Figure 10:
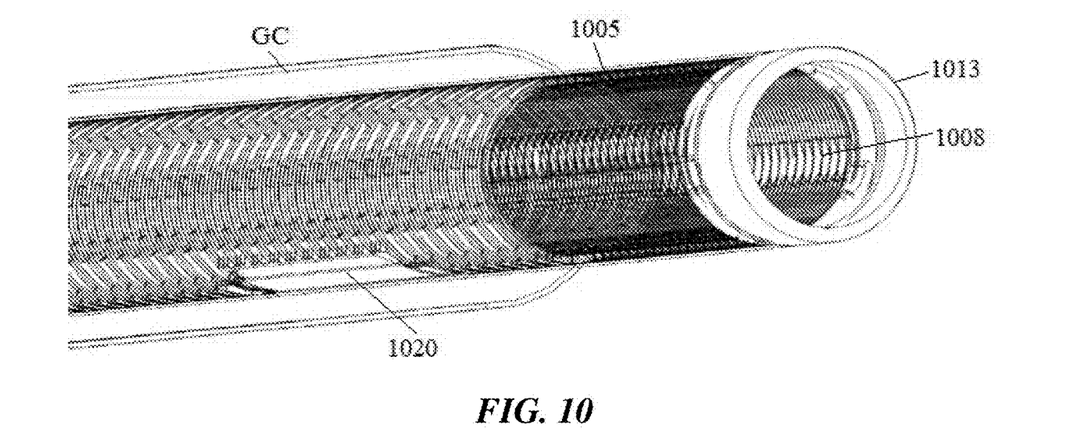
FIG. 10 is a distal perspective view of the device shown in FIG. 7.
Figure 11:
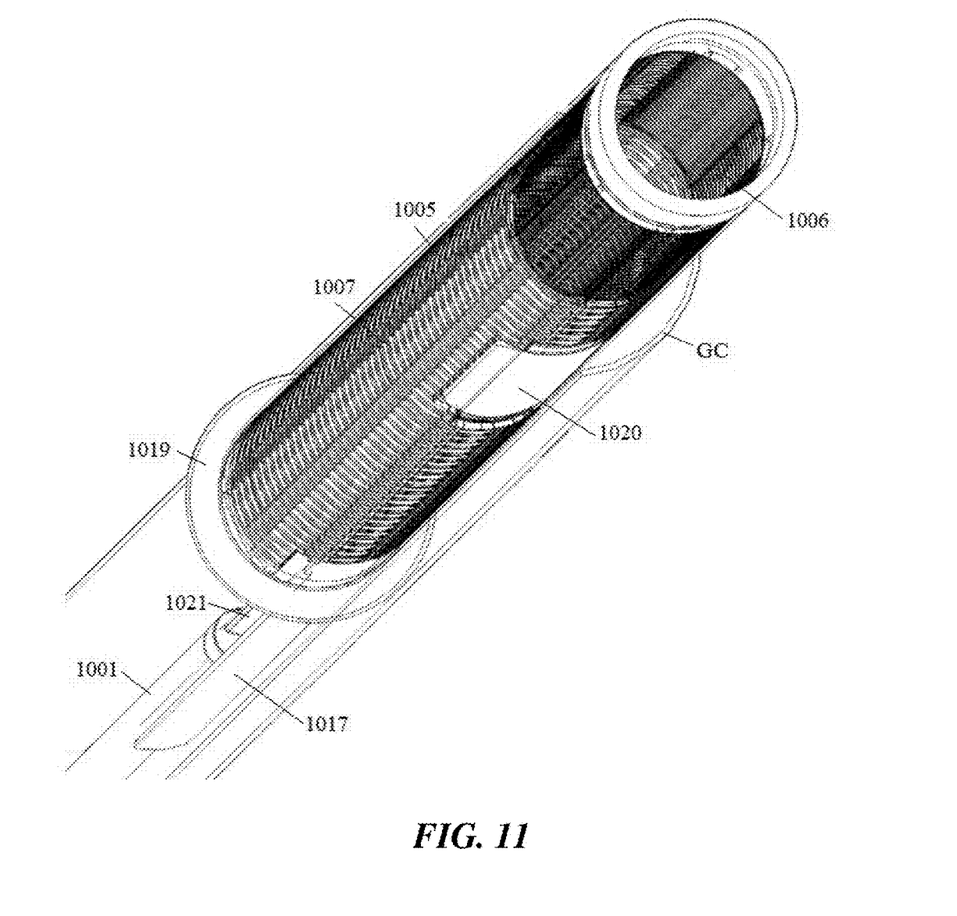
FIG. 11 is an additional distal perspective view of the device shown in FIG. 7.
Figure 12:
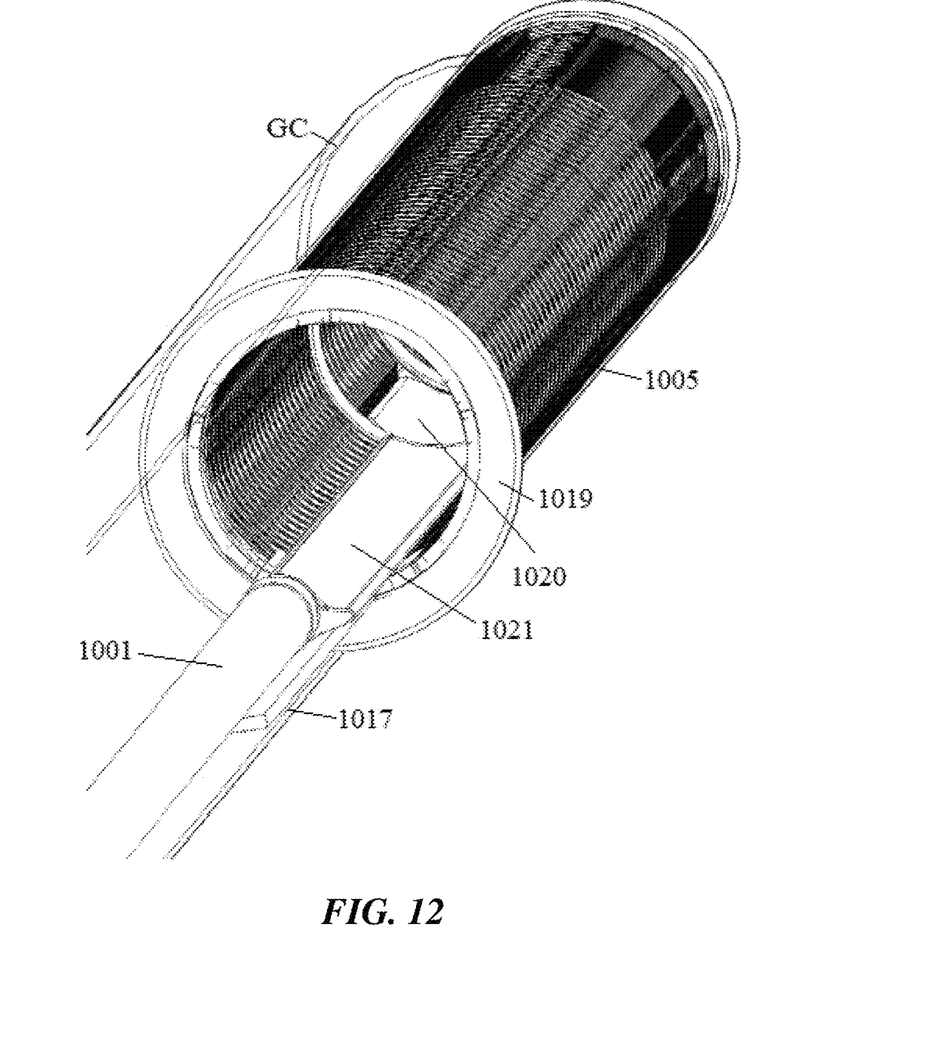
FIG. 12 is a proximal perspective view of the device shown in FIG. 7.
Figure 13:
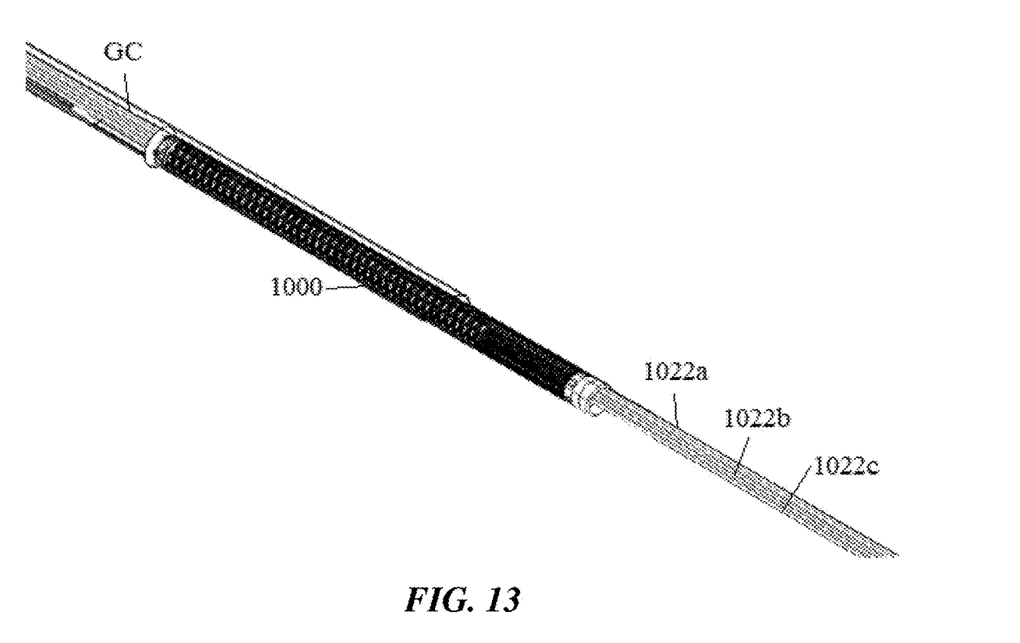
FIG. 13 is an illustration of an example of use for a vascular device constructed in accordance with the principles of the present disclosure.
Figure 14:
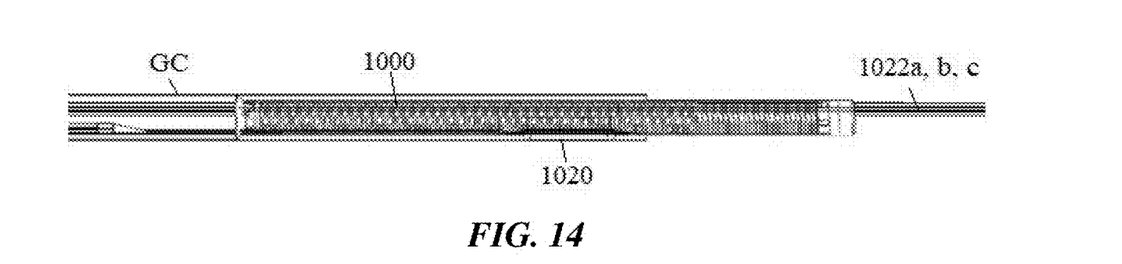
FIG. 14 is a side view of the devices shown in FIG. 13.
Figure 15:
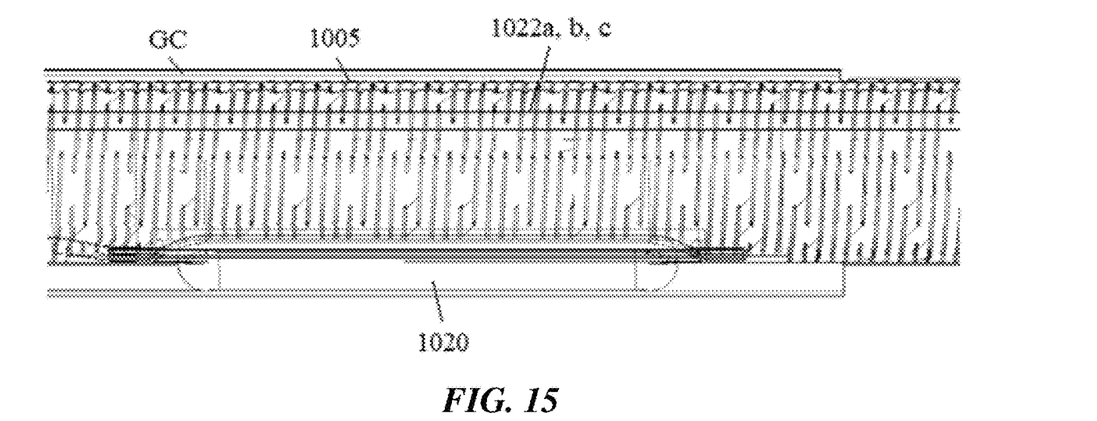
FIG. 15 is a closer side view of the devices shown in FIG. 13.
Figure 16:
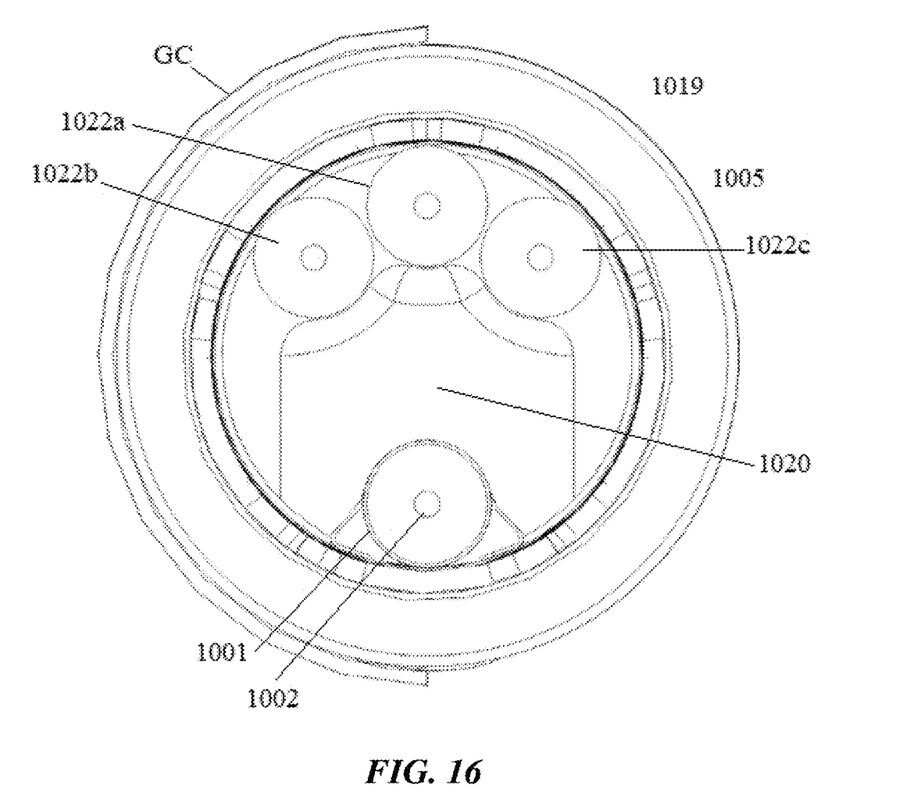
FIG. 16 is a proximal end view of the devices shown in FIG. 13.
Figure 17:
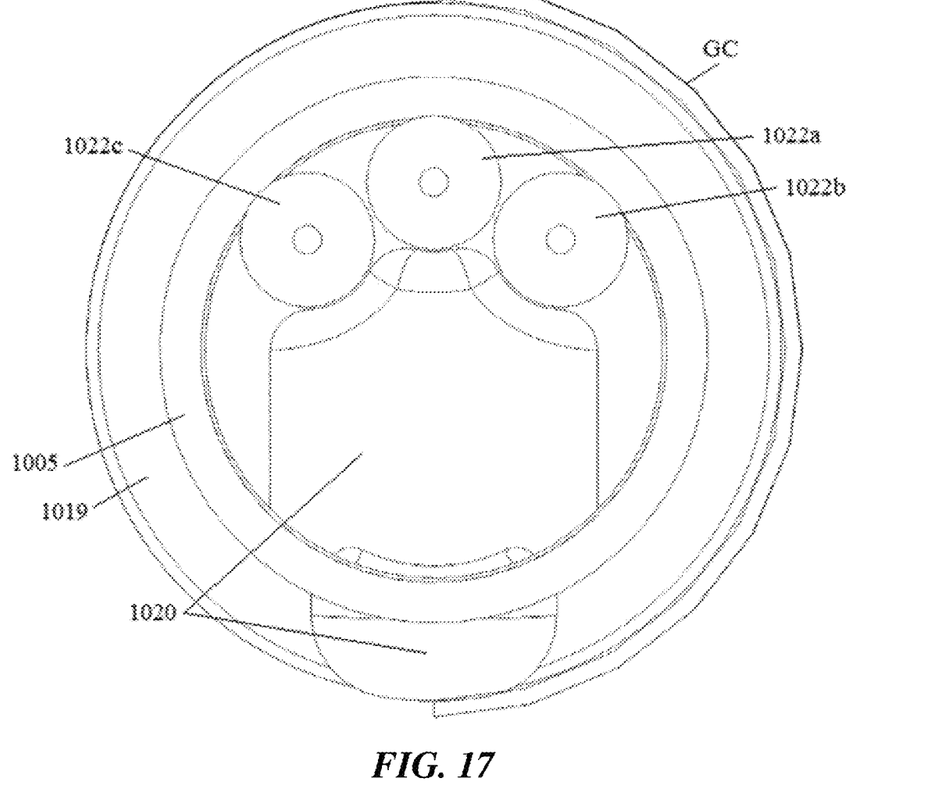
FIG. 17 is a distal end view of the devices shown in FIG. 13.
Figure 18:
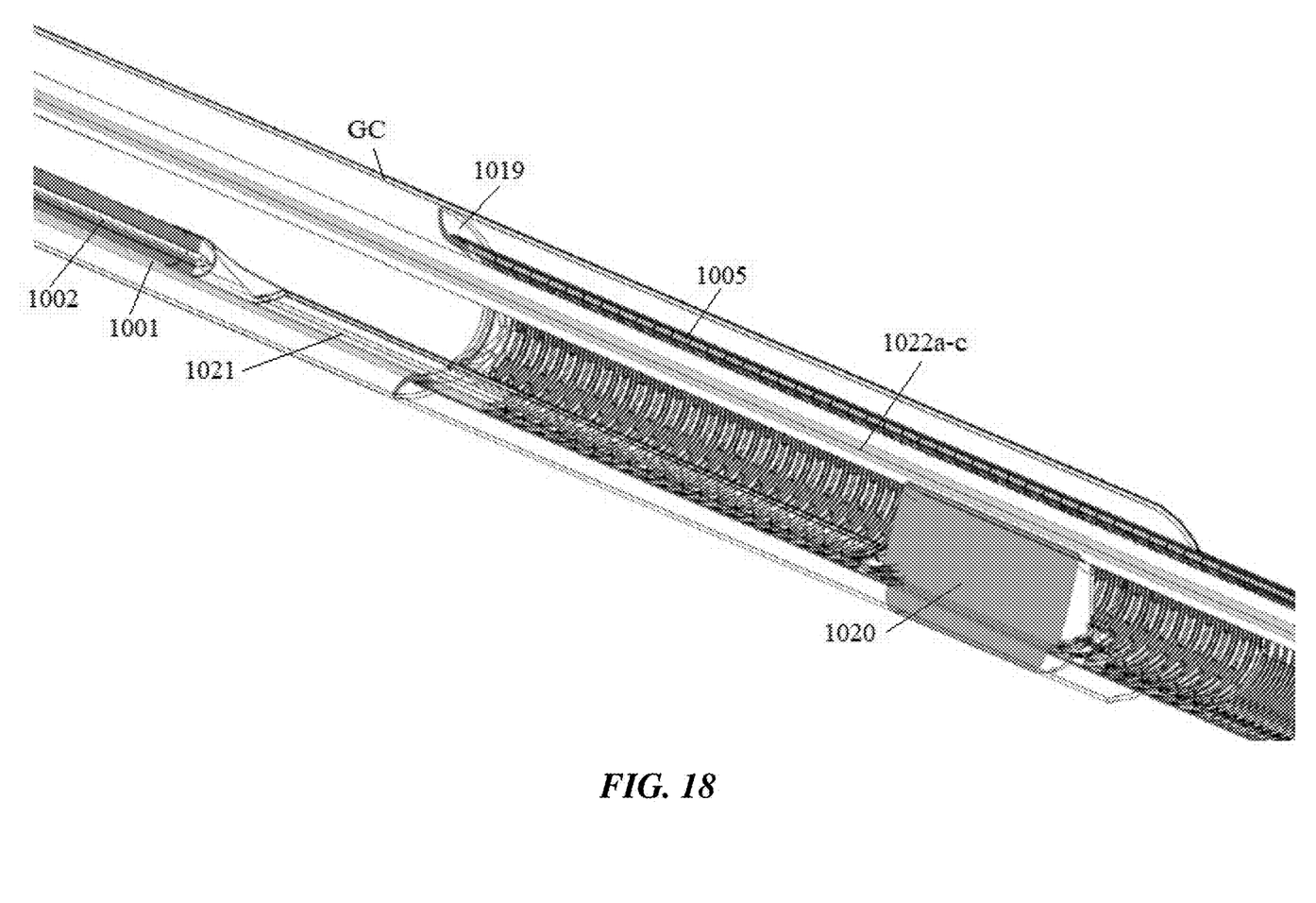
FIG. 18 is a longitudinal cross-sectional view of the devices shown in FIG. 13.
Figure 19:
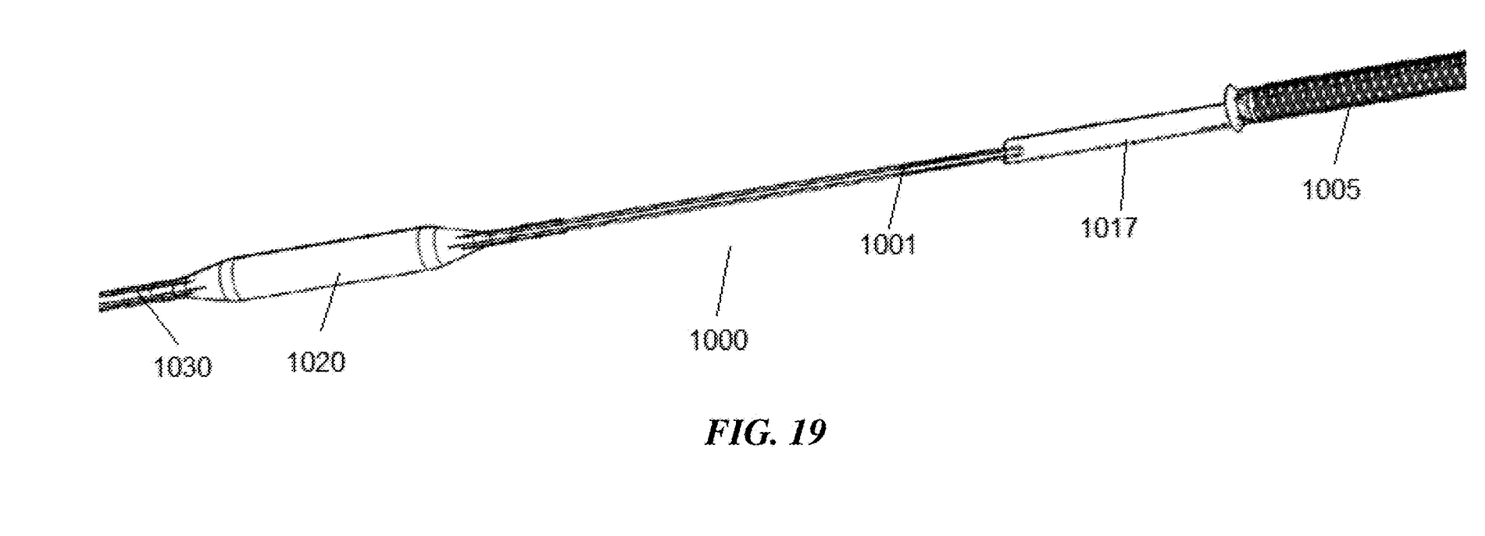
FIG. 19 is an illustration of another example of a vascular device constructed in accordance with the principles of the present disclosure.
Figure 20:
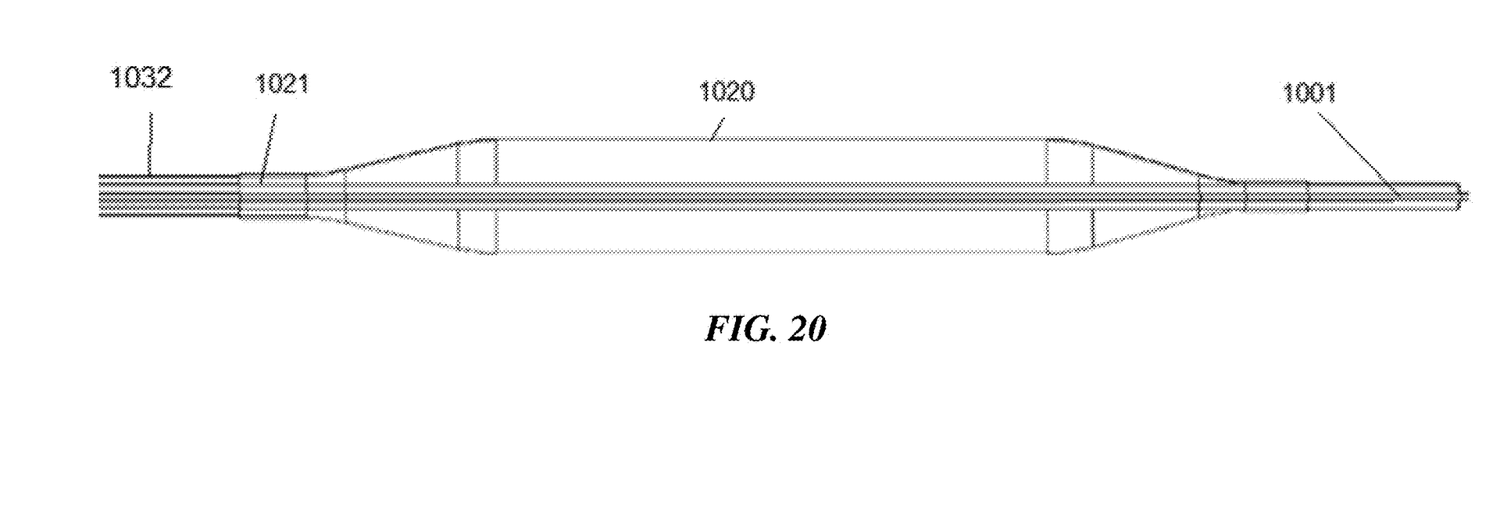
FIG. 20 is a cross-sectional illustration of an inflatable element of the device shown in FIG. 19.

In another example, the device 1000 may include an inflatable element 1020 positioned on the push member 1001, as shown in FIGS. 19-20. This example of the device 1000 may be used to secure one or more auxiliary devices 1022 similarly as described above, with the securing location being proximal of the tube frame 1005 rather than inside the tube frame 1005. In the illustrated example, the inflatable element 1020 may be slidably mounted or coupled to the push member 1001 such that it can be moved along the length of a longitudinal axis of the push member 1001 in proximal and distal directions. For example, the inflatable element 1020 may be attached to a shaft 1030 that is coaxially and/or concentrically mounted on the push member 1001 to provide the slidable movement. The shaft 1030 may include one or more lengths of varying tube along a length thereof, and one or more portions of the inflatable element 1020 may be attached to the shaft 1030 at one or more joints. The shaft may include or define one or more inflation lumens 1032 therein. The lumen(s) 1032 may include one or more segments of an inner diameter of the shaft 1030, one or more tubes positioned within the shaft 1030, and/or one or more spaces between the shaft 1030 and the push member 1001 that provide a fluid path into an interior of the inflatable element 1020. The inflation lumen(s) 1032 may be attached to an inflation source at a proximal end or hub of the device 1000 as described herein.

It will be appreciated by persons skilled in the art that the present disclosure is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the examples disclosed herein are not necessarily exclusive of each other and may be included in a variety of different combinations or configurations without departing from the scope and spirit of the disclosure. A variety of modifications and variations are possible in light of the above teachings without departing from the scope and spirit of the disclosure, which is limited only by the following claims.

What is claimed is:

1. A guide catheter extension, comprising:
a push member having a proximal end and a distal end;
a tube frame coupled to the distal end of the push member, the tube frame defining a lumen having a diameter sufficient to receive an interventional vascular device therethrough; and
an inflatable element coupled to the tube frame, wherein the inflatable element is expandable into the lumen and is expandable outward beyond an exterior surface of the tube frame into a space between the guide catheter extension and a surrounding guide catheter.

2. The guide catheter extension of claim 1, wherein the inflatable element is expandable to occupy between 10% and 90% of a cross-sectional area of the lumen.

3. The guide catheter extension of claim 1, wherein the tube frame defines a window therein through which the inflatable element is expandable outward beyond the exterior surface of the tube frame.

4. The guide catheter extension of claim 1, wherein the push member includes an inflation lumen in fluid communication with an interior of the inflatable element.

5. The guide catheter extension of claim 4, wherein at least a portion of the inflation lumen defines an arcuate cross-section having a radius of curvature equal to a radius of the lumen of the tube frame.

6. The guide catheter extension of claim 1, further comprising a tongue element extending from a proximal segment of the tube frame, wherein the tongue element is directly coupled to the distal end.

* * * * *